United States Patent
Weisshaupt

(10) Patent No.: US 10,556,031 B2
(45) Date of Patent: Feb. 11, 2020

(54) DEVICE FOR COUNTING STERILIZATION CYCLES

(71) Applicant: Aesculap AG, Tuttlingen (DE)

(72) Inventor: Dieter Weisshaupt, Immendingen (DE)

(73) Assignee: Aesculap AG (DE)

( * ) Notice: Subject to any disclaimer, the term of this patent is extended or adjusted under 35 U.S.C. 154(b) by 62 days.

(21) Appl. No.: 15/744,963

(22) PCT Filed: Jul. 20, 2016

(86) PCT No.: PCT/EP2016/067332
§ 371 (c)(1),
(2) Date: Jan. 15, 2018

(87) PCT Pub. No.: WO2017/016958
PCT Pub. Date: Feb. 2, 2017

(65) Prior Publication Data
US 2018/0221526 A1    Aug. 9, 2018

(30) Foreign Application Priority Data

Jul. 27, 2015 (DE) .................. 10 2015 112 205

(51) Int. Cl.
*A61L 2/26* (2006.01)
*G06M 3/12* (2006.01)
(Continued)

(52) U.S. Cl.
CPC ............ *A61L 2/26* (2013.01); *A61B 90/08* (2016.02); *A61L 2/04* (2013.01); *G06M 3/12* (2013.01);
(Continued)

(58) Field of Classification Search
CPC .......... A61L 2/26; A61L 2/04; A61L 2202/24; A61L 2202/14; A61B 90/08;
(Continued)

(56) References Cited

U.S. PATENT DOCUMENTS 5,359,993 A    11/1994 Slater et al.
5,765,413 A *  6/1998 Jung ................. B60R 25/066
                                                    70/201

(Continued)

FOREIGN PATENT DOCUMENTS

DE    4225792 C2    6/1994
DE    69920602 T2   10/2005
(Continued)

OTHER PUBLICATIONS

German Search Report for German Application No. 10 2015 112 205.7, with translation, dated May 13, 2016, 10 Pages.

(Continued)

*Primary Examiner* — Sean E Conley
*Assistant Examiner* — Brendan A Hensel
(74) *Attorney, Agent, or Firm* — RatnerPrestia

(57) ABSTRACT

A device for counting sterilization cycles during the sterilization of medical instruments and devices includes a counter for recording and reproducing a number of sterilization cycles, an actuation unit for sterilization parameter-dependent actuation of the counter, and a locking unit for sterilization parameter-dependent locking the counter. The actuation unit actuates the counter upon exceeding a first threshold sterilization parameter. The locking unit locks the counter after an actuation has been carried out and/or after exceeding a second threshold sterilization parameter, and unlocks the counter after not meeting a third threshold sterilization parameter.

13 Claims, 5 Drawing Sheets

(51) Int. Cl.
*A61B 90/00* (2016.01)
*A61L 2/04* (2006.01)

(52) U.S. Cl.
CPC ............... *A61B 2090/0803* (2016.02); *A61B 2090/0813* (2016.02); *A61L 2202/14* (2013.01); *A61L 2202/24* (2013.01)

(58) Field of Classification Search
CPC .... A61B 2090/0813; A61B 2090/0803; A61B 1/00062; G06M 3/12
See application file for complete search history.

(56) References Cited

U.S. PATENT DOCUMENTS

| | | | |
|---|---|---|---|
| 5,969,315 A | 10/1999 | Schulze | |
| 6,295,330 B1 * | 9/2001 | Skog | ............ A61L 2/28 377/15 |
| 2003/0106930 A1 | 6/2003 | Williams | |
| 2014/0000506 A1 | 1/2014 | Bala et al. | |

FOREIGN PATENT DOCUMENTS

| | | |
|---|---|---|
| DE | 102007039088 A1 | 2/2009 |
| EP | 0979658 A1 | 2/2000 |
| WO | 2014151120 A1 | 9/2014 |

OTHER PUBLICATIONS

International Search Report and Written Opinion for International Application No. PCT/EP2016/067332, dated Oct. 5, 2016, 7 Pages.

* cited by examiner

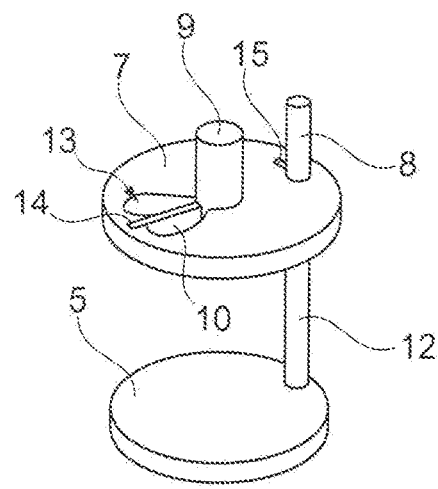
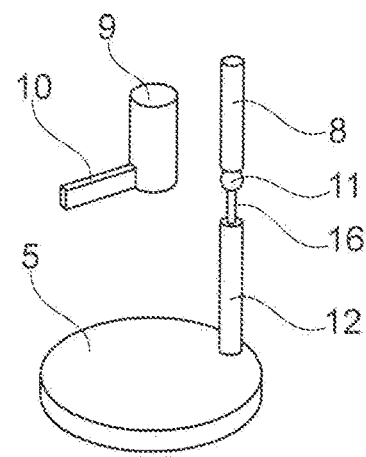
Fig. 3a  Fig. 3b
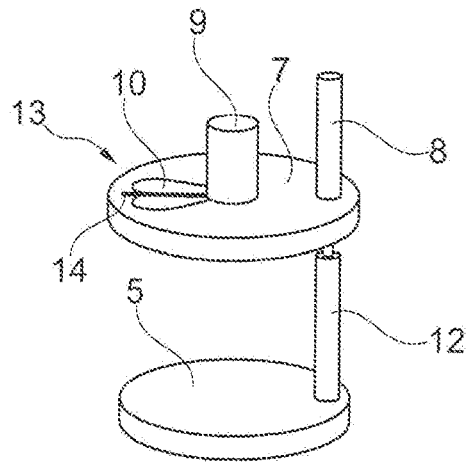
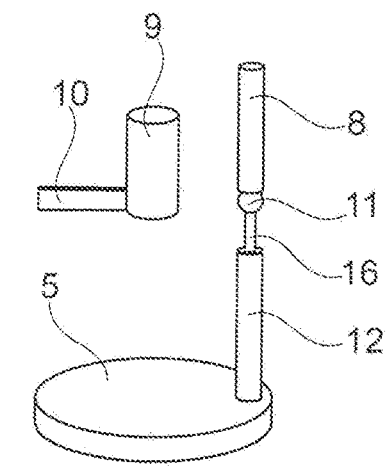
Fig. 3c  Fig. 3d
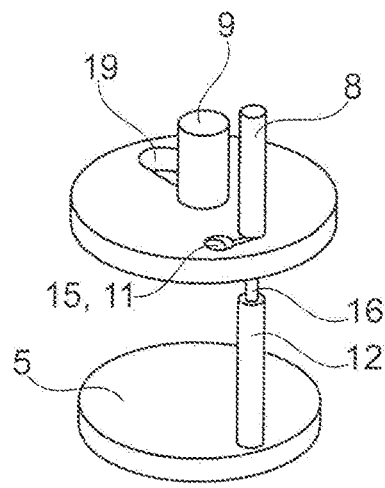
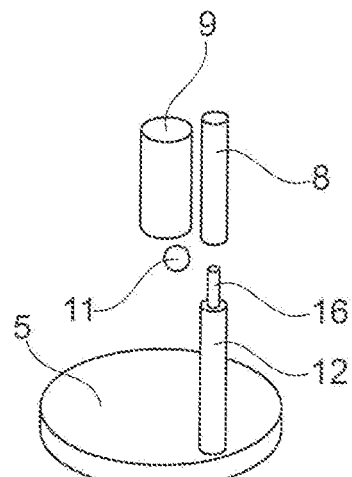
Fig. 3e  Fig. 3f

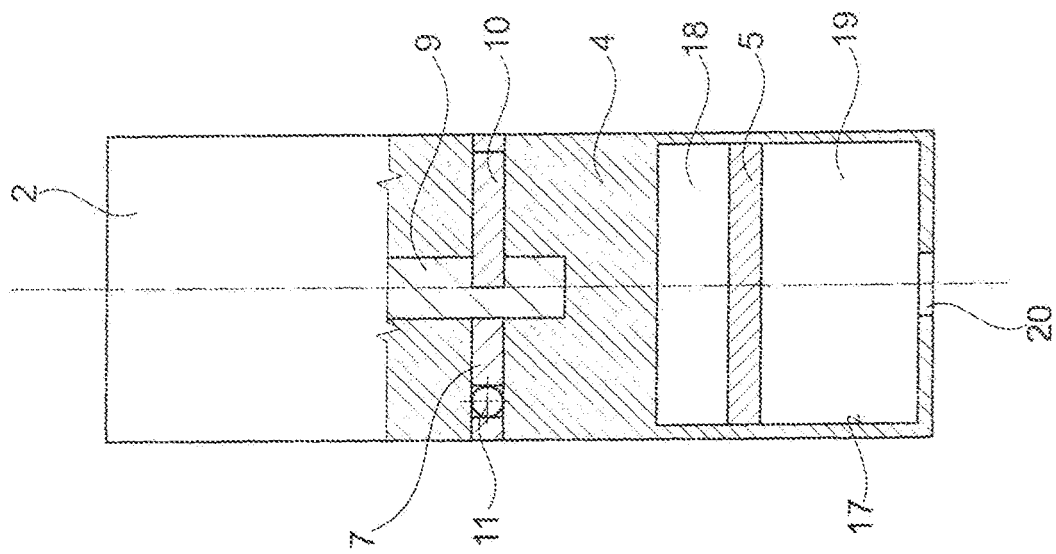
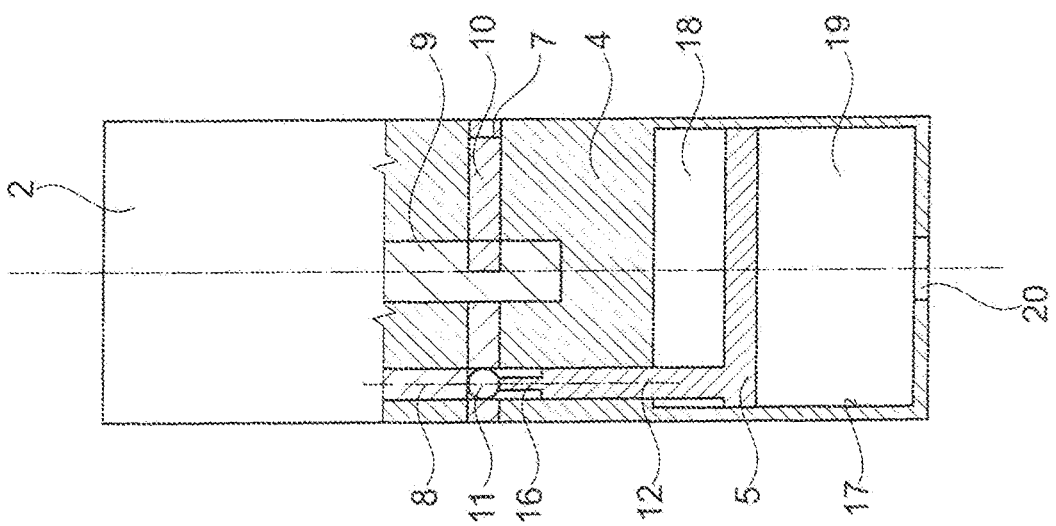
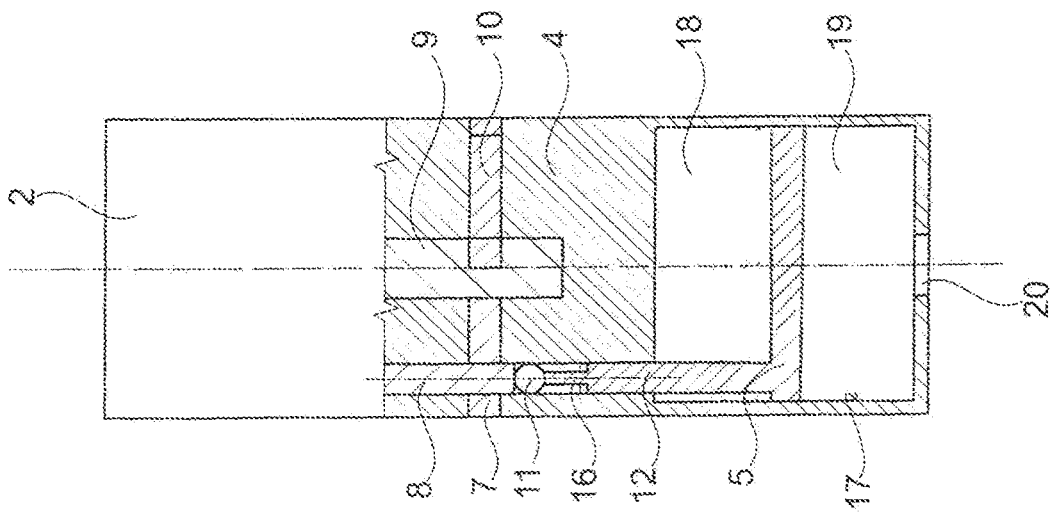

DEVICE FOR COUNTING STERILIZATION CYCLES

RELATED APPLICATIONS

This application is the United States national phase entry of International Application No. PCT/EP2016/067332, filed Jul. 20, 2016, which is related to and claims the benefit of priority of German Application No. 10 2015 112 205.7, filed Jul. 27, 2015. The contents of International Application No. PCT/EP2016/1067332 and German Application No. 10 2015 112 205.7 are incorporated by reference herein in their entireties.

FIELD

The present invention relates to a device for counting sterilization cycles during the sterilization of medical instruments and devices.

BACKGROUND

In clinical daily life, it is often required in particular because of reasons of quality control to detect the number of sterilization cycles to which medical instruments, instrument sets or sterilization containers are subjected. Such recording on the part of the respective specialist staff is performed manually up to now, for example by using tally charts or tables. It is obvious that such a monitoring of the number of sterilization cycles of an instrument is full of uncertainties and unsuitable for verification. It is disadvantageous that it is not possible at present to detect the number of sterilization cycles to which a particular instrument is subjected in a reliable, verifiable and automated manner.

SUMMARY

In connection with this, the present invention is based on the object of providing a possibility and in particular a device by means of which the number of sterilization cycles can be detected and recorded in a simple, reliable, correct, automatic and verifiable manner. It has to be particularly ensured that even a sterilization cycle with a varying pressure and/or temperature course is still detected as one cycle only and wrong multiple detections because of such pressure and/or temperature courses are reliably prevented.

This object is achieved according to the invention by a device for counting sterilization cycles during the sterilization of medical instruments and devices, comprising a counter for recording and reproducing a number of sterilization cycles, an actuation unit for a sterilization parameter-dependent actuation of the counter, and a locking unit for a sterilization parameter-dependent locking of the counter, wherein the actuation unit actuates the counter upon exceeding a threshold sterilization parameter, in particular a threshold sterilization pressure, and the locking unit locks the counter after an actuation has been carried out and/or after exceeding a threshold sterilization parameter, in particular a first threshold sterilization temperature, and unlocks same after falling below a threshold sterilization temperature, in particular a second threshold sterilization temperature.

The invention allows to automatically actuate and lock the counter by utilizing defined parameters during a sterilization process, particularly by using differential pressures and temperatures in a sterilization chamber. The locking device is able to interrupt the actuation of the counter by means of the actuation unit so that it is made sure that the counter is operated only once per each sterilization cycle and the number of sterilization cycles is detected correctly, independently of the respective course. The actuation can be carried out depending on the sterilization pressure, for example, with the process of locking and unlocking being performed as a function of the sterilization temperature. The actuation may alternatively take place depending on the sterilization temperature, with the process of locking and unlocking being performed depending on the sterilization pressure.

The counter preferably has a purely mechanical design. However, it is also possible to use a counter with electronic function. In both cases, its actuation by means of the actuation unit is carried out in a mechanical way. A purely mechanical counter has the advantage that it can be sterilized and conditioned without any problems. The counter may be arranged or mounted on the further components of the device according to the invention, in particular on an interchangeable base. It may alternatively be integrated in the device, for instance received in a common case, or it may form such case.

The actuation unit causes an actuation of the counter which is incremented by one step due to an actuation. By way of example, the actuation unit may change its position relative to the counter and in this way bring about an adjustment of the counter, i.e. a counting step. The actuation unit works according to the invention depending on the sterilization pressure, for example. This means that it brings about an actuation of the counter depending on a pressure prevailing at a sterilization cycle, for example the pressure in a sterilization chamber that acts on the device according to the invention. As a function of the pressure, an actuation of the counter involves the exceeding of a threshold value (threshold sterilization pressure) which can preferably be adjusted by a user of the device, for instance by providing adjustable preload springs or the like. It could be said that the actuation unit causes a counting step of the counter if a certain sterilization pressure has been achieved in the context of a sterilization process.

The locking device is formed such that it locks the counter, after an actuation of the counter by means of the actuation unit, with respect to repeated operations before the end of the sterilization in dependence of parameters of the sterilization process. According to the invention, the locking device works for example depending on the respectively prevailing sterilization temperature to which the device according to the invention is exposed. The locking device can be mechanically held in a position relative to the actuation unit and/or the counter in which an actuation of the latter by the actuation unit is possible. Due to the actuation, this mechanical blockage of the locking device can be canceled so that it is able to move from its initial release position to an arrested position as a function of the control parameters acting on it, in particular depending on the temperature. Alternatively or in addition, the locking device may become unblocked by reaching a threshold parameter, e.g. a threshold sterilization temperature.

A further actuation of the counter by the actuation unit is not possible in the arrested position. The locking device can lock the actuation unit in mechanical manner, for instance in the manner of a bolt so that a relative motion required for the actuation of the counter is not possible. The mentioned first and second threshold sterilization temperatures controlling the locking device may be identical or different. In one embodiment of the invention it may thus be required for a counting step of the counter that the threshold values of the two state variables, namely temperature and pressure, are reached in the sterilization chamber, i.e. take the respectively required threshold values or exceed or fall below them, otherwise there will be no actuation of the counter.

The device according to the invention can be used independently, for instance may be introduced into a sterilization chamber or a sterilization container in addition to instruments to be sterilized. However, it may also be integrated in instruments or sterilization equipment (containers) to be sterilized. Altogether, the invention provides a simple, robust and low-cost possibility in purely mechanical design for detecting and counting the number of sterilization cycles.

The invention makes it possible to achieve in particular the advantages listed in the following: The actuation unit is automatically uncoupled from the counter after a single actuation of the counter so that faulty actuations can be certainly avoided. The counter can be processed in an automatic dishwasher without hesitation and without the risk of erroneously recording further counting steps. The counter can be used independently and placed in or on a sieve basket. The counter can be integrated in a front panel of a sterilization container. The counter can be zeroed/reset in a simple manner.

Advantageous embodiments of the invention are explained more precisely in the following.

In one embodiment of the invention, the actuation unit comprises a piston/cylinder unit having a chamber that can be acted upon by the sterilization pressure. The piston and the cylinder, for actuating the counter, may be capable of being positioned relative to each other depending on the sterilization pressure. Apart from the chamber pressurized with the sterilization pressure, the piston/cylinder unit may comprise a pressure chamber. This pressure chamber may be acted upon with a nominal pressure, as a counterpressure counteracting the sterilization pressure, which can be preferably adjusted by a user. By adjusting the counterpressure in the pressure chamber, the respective response pressure (threshold value of the sterilization pressure) can be set.

A further embodiment of the invention is characterized in that the locking unit comprises a disc which can be moved, in particular rotated with respect to the piston/cylinder unit and has a passage for the actuation element. If the passage and the actuation unit are aligned relative to each other, an actuation of the counter is possible. The actuation unit is locked in other positions of the disc relative to the actuation unit so that an actuation is not possible. The disc which also can be referred to as control disc then acts on the actuation unit in the manner of a mechanical lock. Preferably, the disc can be positioned with respect to the actuation element in terms of rotation.

The locking device may comprise in particular a bimetal element. The latter can be deformed depending on the sterilization temperature between a first shape and a second shape. In this way, the position of the disc relative to the actuation unit can be determined by the deformation of the bimetal element. The disc may thus be kinetically coupled to the bimetal element. In particular, the disc may adopt a first position when the bimetal element is in the first shape and may adopt a second position when the bimetal element is in the second shape. The counter may be decoupled from the actuation unit in the first shape, i.e. the disc is in its blocking or locking position. In the second shape, the counter may be coupled to the actuation unit, i.e. the disc is in its release position. The bimetal element may be particularly formed in such a manner that it is deformed from its first shape into its second shape upon exceeding a first threshold sterilization temperature. It may be deformed from its second shape back into its first shape when falling below a second threshold sterilization temperature. The first and the second threshold sterilization temperature may be identical or different.

According to an embodiment of the invention, the actuation unit may further comprise a stud for actuating the counter. The control disc may be provided with a passage for such a stud. When the control disc is in the first position, the passage is preferably positioned so as to be in alignment with the stud, allowing an actuation of the counter. When the control disc is in the second position, the stud is locked, cannot extend through the passage and an actuation of the counter is not possible. In one embodiment of the invention, the stud is formed as a piston rod and indirectly connected to the piston of the piston/cylinder unit, preferably directly connected to it. In a similar way, the counter may comprise a pin or stud. The actuation unit may be able to indirectly or directly actuate it. The counter stud may engage a cutout of the control disc and in this way block the latter in its release position. If the counter stud and the actuation unit engage the same cutout of the control disc, the latter can get unblocked in the context of an actuation of the counter in a particularly easy way.

A force transmission element, preferably a roller or a ball, may be arranged between the actuation unit and the counter in the passage of the control disc. This is particularly advantageous with an actuation unit that has a stud/piston. The force transmission element advantageously delivers the actuation force required for the actuation of the counter, but uncouples other forces and moments so that an unwanted erroneous stress on the counter can be prevented. In one embodiment comprising a pressure chamber, the latter is not blocked which means that the piston can move freely in the cylinder. This preserves the complete system.

In one embodiment of the invention, the passage in the control disc may comprise a first portion having a first width and a second portion having a width smaller than that of the first portion. The three transmission element may be arranged in particular in the first portion. The width of the force transmission element is preferably larger than the width of the second portion. According to one embodiment, the stud may have a width which is larger than the width of the first portion. The stud's end portion facing the force transmission element may have a reduced width which is smaller than that of the second portion.

The control disc is preferably rotatably supported on a guide bolt. It may comprise in particular a central opening, especially a through-hole in which the guide bolt is received to be rotatable relative to the disc. One end section of the bimetal element is preferably arranged on the guide bolt and may protrude from it in particular in radial direction. With the other end section opposite to the one end section, it is connected to the control disc.

The cylinder preferably comprises a cylinder housing in which the piston is received so as to be axially positionable. Furthermore, the control disc is received in said cylinder housing so as to be able to rotate. The counter is received at the end side on or in the cylinder housing and so as to be not positionable relative to the cylinder housing. The counter according to the invention may have any design, for example mechanical or digital. A mechanical counter is, however, preferred due to its ruggedness.

In brief, it can be stated that the invention combines a mechanical counter with a hermetically sealed pressure chamber for its actuation. The chamber is filled with a suitable gas or air mixture. The gas expands or contracts with an excess pressure and an underpressure in the sterilization chamber, respectively. In order to utilize these conditions of the gas, the chamber may be provided with an elastic diaphragm. In one embodiment of the invention, the combination of cylinder/piston is able to function so exactly that it is air-tight or gas-tight. The diaphragm or the piston causes a balancing of pressure changes and thus is inevitably subject to positional changes, i.e. travels a certain distance for instance. This positional change is used to switch or operate the counter.

During a sterilization process it may happen that overpressure and underpressure alternate several times so that there may be several changes in the position of the piston or membrane. To prevent that the counter is repeatedly actuated with such a pressure course during a sterilization process, the locking device and in particular the bimetal strip cancels the control function of the pressure chamber. This is performed via the control disc which for preventing an actuation of the counter is positioned by means of a deformation of the bimetal strip. The actuation unit, particularly the actuation stud or pin of the counter, is in the upper position now and is blocked from moving downward by the control disc. It waits now for moving again to the initial position in order to complete the switching process. Since the temperature usually does not fall below 80° C. during a sterilization process, the bimetal element reacts only after completion of the process and returns into its original shape if the room temperature is almost reached, for example. In its original shape, the bimetal element returns the control disc back to its original position in which the actuation unit and in particular the actuation stud is released. It is important that the pressure chamber is not blocked but is able to adapt to respectively prevailing pressure conditions and pressure differences. This preserves the complete system and makes it robust. The counter reacts virtually purely digitally although it is mechanical and may be in particular commercially available. With a counter of this type, a one-time operation and releasing of the actuation pin results in increasing the counting unit by one digit. The bimetal element is controlled by temperature variations in the sterilization chamber (by having influence on its shape or form), while pressure changes in the chamber control the pneumatic piston, i.e. displace the latter.

BRIEF DESCRIPTION OF THE DRAWING FIGURES

Further features and advantages of devices in accordance with the present invention will be apparent from the following exemplary and non-limiting description of embodiments on the basis of Figures. These are of schematic nature only and merely serve the purpose of understanding embodiments of the invention. In the Figures.

Figure 5:
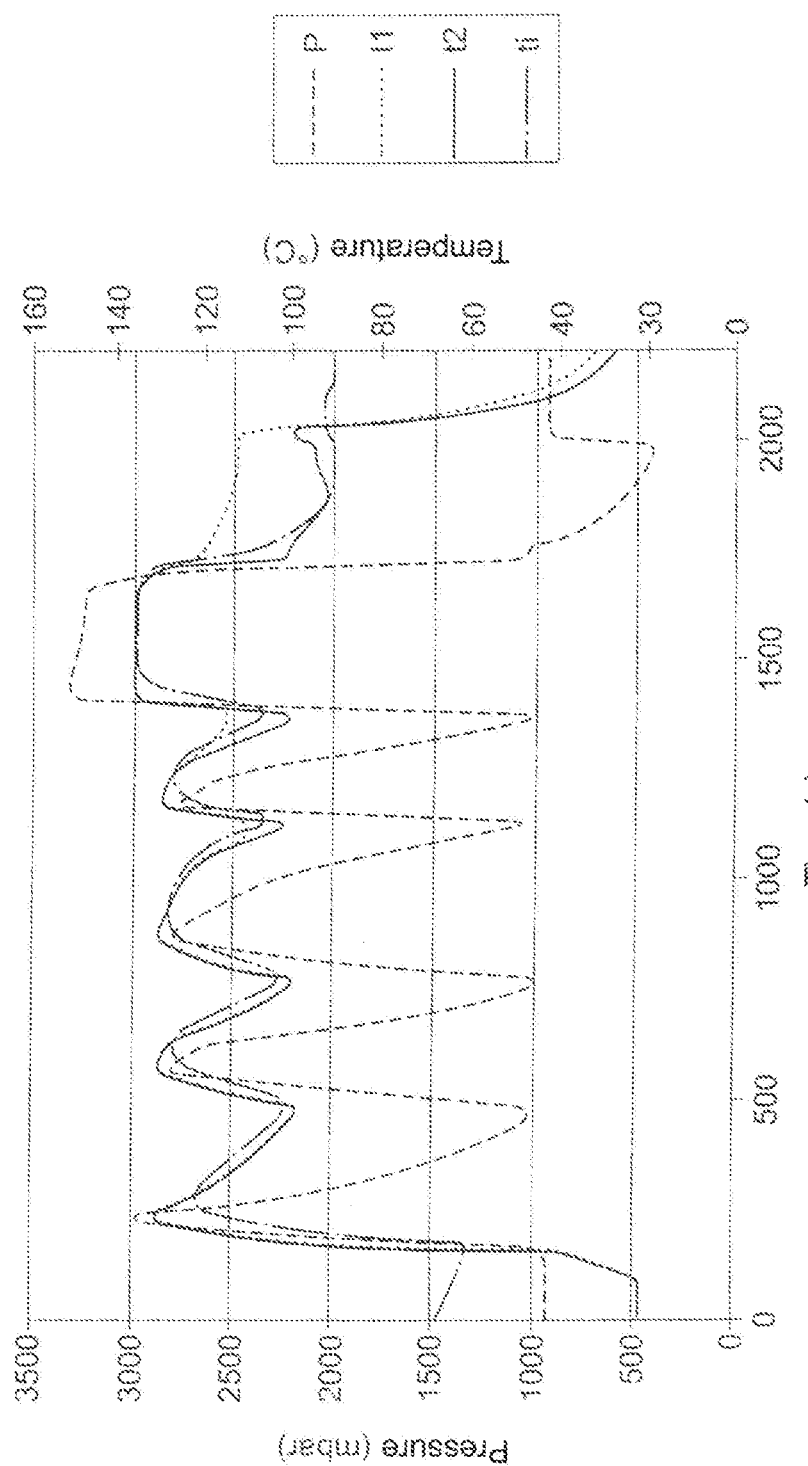

FIGS. 3a to 3f each show, in exposed fashion and in a perspective view, selected components of the device in different functional positions, FIGS. 4a to 4c each show a cross-section of the device in different functional positions and FIG. 5 shows a diagram of pressure versus time as an example of a sterilization cycle in a fractionated vacuum method.

DETAILED DESCRIPTION

Figure 1:
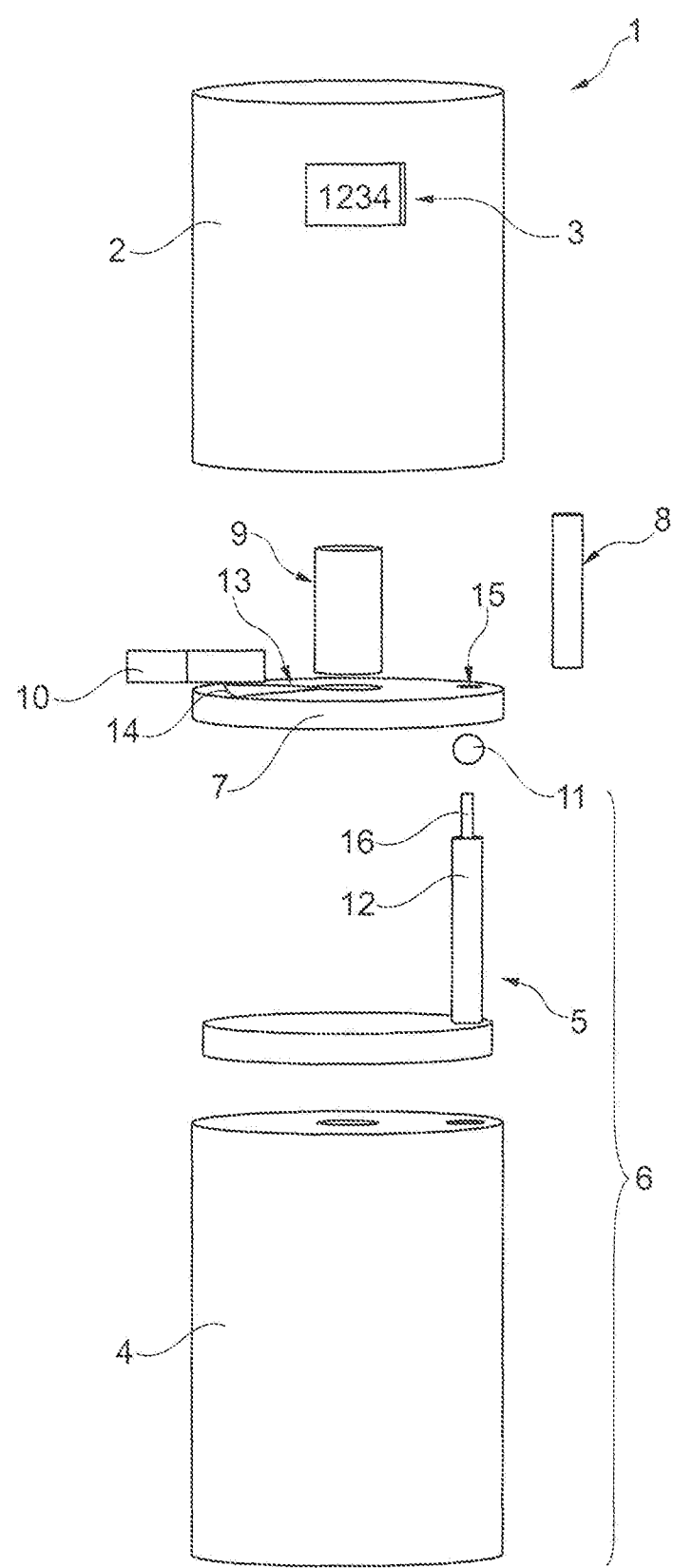
FIG. 1 is a schematic exploded view of an embodiment of the device.
Figure 2:
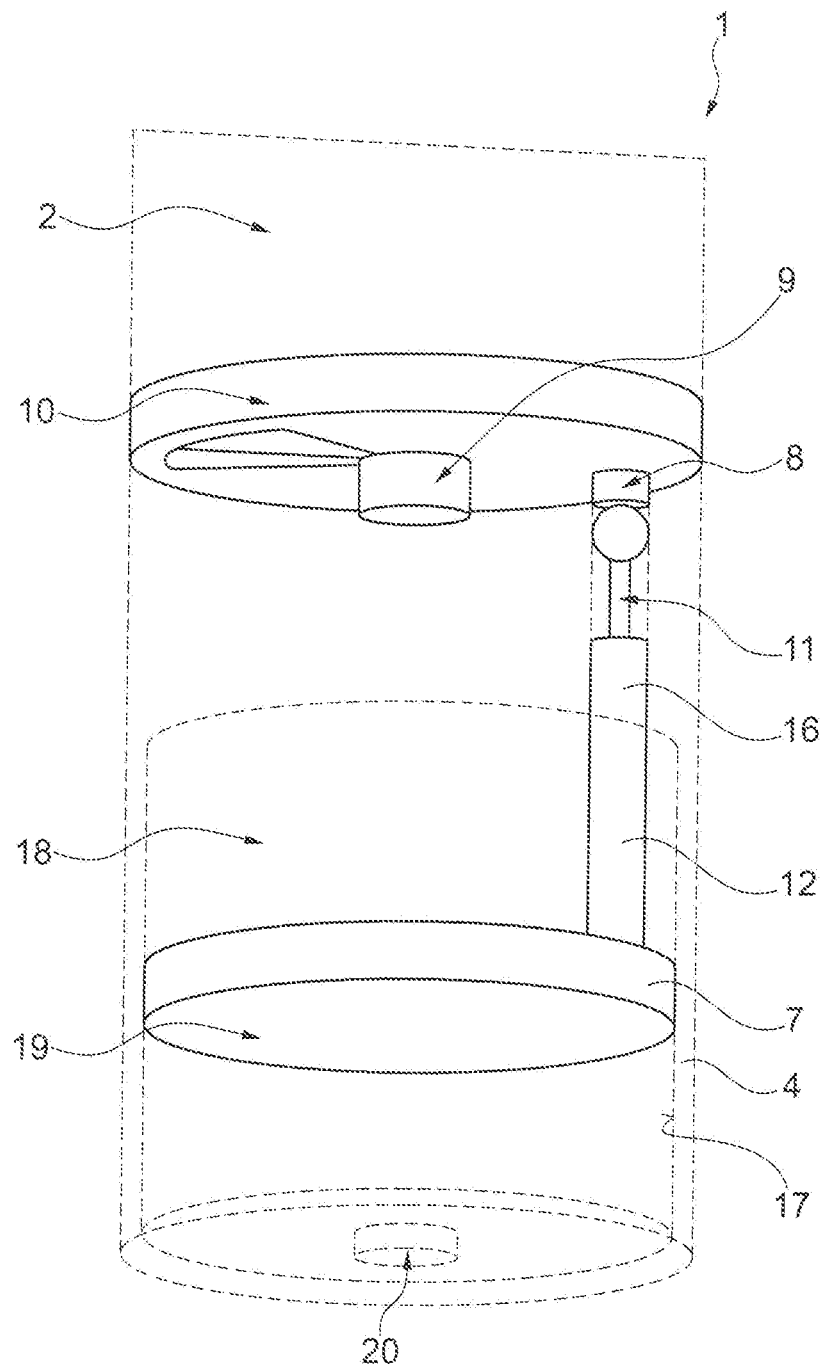
FIG. 2 is a schematic perspective view of the device of FIG. 1.

FIG. 1 shows an embodiment of the device 1 in a perspective exploded view. The device comprises a mechanical counter 2 with a counter display 3, a cylinder 4 which together with a piston 5 forms a piston/cylinder unit as an actuation unit 6, and a control disc 7. Further components of the device include a counter pin 8, a guide bolt 9 by means of which the control disc 7 is rotatably supported on the counter 2, a bimetal element 10, a ball 11 as a force transmission element and a piston stud 12.

The further description is made with reference to FIGS. 1, 2, 3a to 3f and 4. The counter 2 comprises a central seating (not shown in the Figures) in which the guide bolt 9 is fixedly received, e.g. is glued therein. A cutout is laterally machined in the guide bolt (see for example FIGS. 4a to 4c) in which the bimetal element 10 is fastened such that it protrudes from the guide bolt 9 in radial direction. Radially outside its central cutout, the control disc 7 has a recess 13 as a seating for the bimetal element 10. The recess 13 is formed to be approximately heart-shaped as is indicated in FIG. 3, so that it has a clamping slot 14 for the bimetal element 10 in a radially outer area. In particular FIGS. 4a to 4c show that the bimetal element 10 and the disc 7 are arranged on the guide bolt at the same level as seen in axial direction.

The control disc 7 further comprises a passage opening 15 that can be seen in FIGS. 3e and 4a to 4c. The ball 11, the counter pin 8 or the piston stud 12 extend through said passage opening depending on the functional position of the device. The passage opening 15 is approximately shaped like a keyhole and comprises a wide portion with a diameter which is slightly wider than the respective diameters of ball 11, counter pin 8 and piston stud 12 and is penetrated by these elements, and a tangentially adjoining portion with a small width. The width of the latter is smaller than the width of the piston stud 12, but wider than that of a piston pin 16 formed on the end side of the piston stud 12.

The cylinder 4 receives the piston 5 including the piston stud 12 integrally formed thereon, together with the piston pin 16 (see FIGS. 4a to 4c). It rests against an internal wall 17 of the cylinder 4 in sealing manner and can move therein in axial direction. A counterpressure chamber 18 on the one hand a sterilization pressure chamber 19 on the other hand are formed between the piston 5 and the cylinder 4. The counterpressure chamber 18 is closed hermetically by the sealing contact between piston 5 and cylinder 4. The sterilization pressure chamber 19, however, is provided with an opening 20 which establishes a connection to the atmosphere surrounding the device. Via this opening 20, the external pressure surrounding the device 1 always prevails in the sterilization chamber 19, which in the event of a sterilization is the respective sterilization pressure.

FIGS. 3a to 3e show the piston 5 together with counter pin 8, piston stud 12, piston pin 16, disc 7, bimetal element 10, ball 11 and guide bolt 9 each in exposed fashion and in a perspective view, with the control disc 7 being not represented in the FIGS. 3b, 3d and 3f for a better overview. It is to be noted that the Figures show the mentioned elements from slightly different angles.

FIGS. 3a and 3b as well as FIG. 4a show a first operating state in which the temperature in a (not represented) sterilization chamber is about 22° C., the counterpressure in the counterpressure chamber 18 is approximately 1 bar and the sterilization pressure in the sterilization pressure chamber is likewise approximately 1 bar. This is the condition at the beginning of a sterilization cycle. The bimetal element 10 has its original shape with these parameters (second shape). The passage opening 15 is in alignment with the piston stud 12, the piston pin 16 and the ball 11. As shown in FIG. 4a, the counter pin 8 which is preloaded in downward direction toward the pressure chambers 18, 19 by means of a spring extends through the passage opening 15 and rests against the piston pin 16 and the piston stud 12 via the ball 11.

FIGS. 3c and 3d as well as 4b show a second operating state in which the temperature in a (not represented) sterilization chamber is higher than 22° C., the counterpressure in the counterpressure chamber 18 is higher than 1 bar and the sterilization pressure in the sterilization pressure chamber is also higher than 1 bar. In this condition, the pressure (sterilization pressure) in the pressure cylinder 19 and in the sterilization chamber has increased with respect to its original value and with respect to the pressure in the counterpressure chamber 18. The pneumatic piston 5 moves upwards to the counterpressure chamber 18 because of the difference in pressure, so that the gas contained therein is compressed until a pressure balance is approximately reached. Specifically, the following applies to the pressure balance:

$$P_{sterilization\ chamber} = P_{counterpressure\ chamber} + F_{counter\ pin\ spring} + \text{friction}$$

The piston stud 12 pushes the spring-loaded counter pin 8 via the piston pin 16 and the ball 11 upwards toward the counter whereby a counting step is initiated. The control disc 7 is released by the counter pin 8 now and can turn around the guide bolt 9. As soon as the counter pin 8 releases the disc 7, the ball 11 is in the passage opening 15 and is entrained by the disc 7 when the latter rotates around the guide bolt 9 (see for example FIGS. 3d and 3e). A rotation of the disc 7 as well as an axial movement of the piston 5 including the piston pin 16 is possible without conflicts since the piston pin 16 has a width which is smaller than the width of the narrow portion of the keyhole-shaped passage opening 15. FIGS. 3c and 3d as well as FIG. 4b show the mentioned elements of the device 1 in a condition when moved in axial direction, but not rotated radially.

FIGS. 3e and 3f as well as 4c show a third operating state in which the temperature in a (not represented) sterilization chamber is approximately between 60° C. and 134° C., the counterpressure in the counterpressure chamber 18 ranges from approx. 0.2 bar to 3 bar (absolute pressure) and the sterilization pressure in the sterilization pressure chamber likewise ranges from approx. 0.2 bar to 3 bar. The bimetal element 10 is deformed because of the considerably increased temperature and exerts a torque on the control disc 7. The control disc 7 is thus rotated in radial direction, while the ball 11 gets separated from the piston pin 16 and the counter pin 8, which means that these elements are not in mutual contact any more and no force can be transferred in axial direction any more, independently of the position of the piston 5. In this way the force transmission from the actuation unit 6 into the counter 2 is interrupted. The piston pin 16 provided on the pneumatic piston 5 has a smaller diameter at the distal end, so that it can penetrate the groove of the control disc 7 without touching the counter pin 8. The counter pin 8 is held in position by the control disc 7 until the temperature has fallen back to room temperature again and the bimetal element 10 moves the control disc 7 back to its original position shown in FIGS. 3a to 3d as well as 4a and 4h.

The courses of the parameter values of temperature and pressure are exemplarily shown in FIG. 5 for the procedures described above.

The invention claimed is:

1. A device for counting sterilization cycles during the sterilization of medical instruments and medical devices, the device comprising:

a counter for recording and reproducing a number of sterilization cycles;
an actuation unit for a sterilization parameter-dependent actuation of the counter; and
a locking unit for a sterilization parameter-dependent locking of the counter, wherein
the actuation unit comprises a stud/pin for actuating the counter and a piston/cylinder unit having a chamber that can be acted upon by a sterilization pressure, the piston/cylinder unit comprising a piston and a cylinder being capable of being positioned relative to each other depending on the sterilization pressure; and wherein
the locking unit comprises a disc which can be moved with respect to the piston/cylinder unit and has a passage for the actuation unit, said passage being positioned so as to be in alignment with the stud/pin and allowing an actuation of the counter when the disc is in a first position and locks the stud/pin and prevents the counter from being activated when the disc is in a second position.

2. The device according to claim 1, wherein the actuation unit actuates the counter upon exceeding a first threshold sterilization pressure, and
wherein the locking unit locks the counter after an actuation has been carried out and/or after exceeding a first threshold sterilization temperature, and unlocks the counter after falling below a second threshold sterilization temperature.

3. The device according to claim 1, wherein the locking unit comprises a bimetal element which is deformed between a first shape and a second shape depending on a sterilization temperature,
wherein the bimetal element decouples the counter from the actuation unit when the bimetal element is in the first shape, and
wherein the bimetal element couples the counter to the actuation unit when the bimetal element is in the second shape.

4. The device according to claim 3, wherein the disc is kinetically coupled to the bimetal element and adopts a first position when the bimetal element is in the first shape and adopts a second position when the bimetal element is in the second shape.

5. The device according to claim 1, wherein a force transmission element is arranged between the actuation unit and the counter in the passage of the disc.

6. The device according to claim 5, wherein the passage in the disc comprises a first portion having a first width and a second portion having a second width smaller than the first width.

7. The device according to claim 6, wherein the force transmission element is arranged in the first portion and the width of the force transmission element is larger than the second width of the second portion.

8. The device according to claim 7, wherein the stud has a width which is larger than the first width of the first portion, wherein the stud has an end portion facing the force transmission element, and wherein the end portion has a reduced width which is smaller than the second width of the second portion.

9. The device according to claim 3, wherein the disc is rotatably supported on a guide bolt and comprises a central opening in which the guide bolt is received to be rotatable relative to the disc.

10. The device according to claim 9, wherein a first end section of the bimetal element is arranged on the guide bolt and a second end section of the bimetal element is connected to the disc.

11. The device according to claim 1, wherein the cylinder comprises a cylinder housing in which the piston is received to be axially positionable, and in which the disc is rotatably received, with the counter being received at an end side on or in the cylinder housing.

12. The device according to claim 1, wherein the actuation unit actuates the counter upon exceeding a first threshold sterilization parameter, and the locking unit locks the counter after an actuation has been carried out and/or after exceeding a second threshold sterilization parameter, and unlocks the counter after falling below a third threshold sterilization parameter.

13. A device for counting sterilization cycles during the sterilization of medical instruments and medical devices, the device comprising:
- a counter for recording and reproducing a number of sterilization cycles;
- an actuation unit for a sterilization parameter-dependent actuation of the counter; and
- a locking unit for a sterilization parameter-dependent locking of the counter,
- wherein the actuation unit actuates the counter upon exceeding a first threshold sterilization parameter, and
- the locking unit locks the counter after an actuation has been carried out and/or after exceeding a second threshold sterilization parameter, and unlocks the counter after falling below a third threshold sterilization parameter,
- wherein the actuation unit actuates the counter upon exceeding a first threshold sterilization pressure,
- wherein the locking unit locks the counter after an actuation has been carried out and/or after exceeding a first threshold sterilization temperature, and unlocks the counter after falling below a second threshold sterilization temperature,
- wherein the actuation unit comprises a piston/cylinder unit having a chamber that can be acted upon by a sterilization pressure, the piston/cylinder unit comprising a piston and a cylinder for actuating the counter and being capable of being positioned relative to each other depending on the sterilization pressure,
- wherein the locking unit comprises a disc which can be moved with respect to the piston/cylinder unit and has a passage for the actuation unit,
- wherein the locking unit comprises a bimetal element which is deformed between a first shape and a second shape depending on a sterilization temperature,
- wherein the bimetal element decouples the counter from the actuation unit when the bimetal element is in the first shape,
- wherein the bimetal element couples the counter to the actuation unit when the bimetal element is in the second shape,
- wherein the disc is kinetically coupled to the bimetal element and adopts a first position when the bimetal element is in the first shape and adopts a second position when the bimetal element is in the second shape, and
- wherein the actuation unit comprises a stud/pin for actuating the counter, said passage being positioned so as to be in alignment with the stud/pin and allowing an actuation of the counter when the disc is in the first position and locks the stud/pin and prevents the counter from being activated when the disc is in the second position.

* * * * *